(12) United States Patent
Fautz et al.

(10) Patent No.: US 11,408,957 B2
(45) Date of Patent: Aug. 9, 2022

(54) METHOD AND APPARATUS FOR TRIGGERING MAGNETIC RESONANCE RECORDINGS WITH OBJECT MOVEMENTS

(71) Applicant: Siemens Healthcare GmbH, Erlangen (DE)

(72) Inventors: Hans-Peter Fautz, Forchheim (DE); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 576 days.

(21) Appl. No.: 16/374,986

(22) Filed: Apr. 4, 2019

(65) Prior Publication Data

US 2019/0310340 A1    Oct. 10, 2019

(30) Foreign Application Priority Data

Apr. 4, 2018    (DE) .......................... 102018205077.5

(51) Int. Cl.
| | | |
|---|---|---|
| *G01R 33/563* | (2006.01) | |
| *G01R 33/567* | (2006.01) | |
| *G01R 33/48* | (2006.01) | |
| *G01R 33/565* | (2006.01) | |
| *G01R 33/561* | (2006.01) | |

(Continued)

(52) U.S. Cl.
CPC .......... *G01R 33/5673* (2013.01); *A61B 5/024* (2013.01); *A61B 5/055* (2013.01); *A61B 5/113* (2013.01); *A61B 5/318* (2021.01); *A61B 5/7207* (2013.01); *A61B 5/7292* (2013.01);
(Continued)

(58) Field of Classification Search
CPC ............ G01R 33/5673; G01R 33/4828; G01R 33/56509; G01R 33/5617; G01R 33/5602; G01R 33/586; A61B 5/318; A61B 5/7292; A61B 5/113; A61B 5/7207; A61B 5/024; A61B 5/055; A61B 5/7285
See application file for complete search history.

(56) References Cited

U.S. PATENT DOCUMENTS 4,766,381 A * 8/1988 Conturo ............... G01R 33/482
                                                    324/309
5,429,134 A * 7/1995 Foo .................... G01R 33/5607
                                                    324/307
(Continued)

OTHER PUBLICATIONS

Pooley et al., AAPM/RSNA Physics Tutorial for Residents Fundamental Physics of MR Imaging, RadioGraphics 2005; 25:1087-1099.*

(Continued)

*Primary Examiner* — Bo Joseph Peng
(74) *Attorney, Agent, or Firm* — Banner & Witcoff Ltd.

(57) ABSTRACT

High-quality magnetic resonance (MR) recordings are triggered with movements of an object, for example the heartbeat. In a method and apparatus for obtaining raw data reconstruction for an MR image, a spin-echo-based sequence is executed that includes applying a static magnetic field and applying a magnetization pulse train. A movement of the object to be imaged is detected and a target contrast for two tissue types of the object is prespecified. The repetition time of the pulse train is set in dependence on the movement of the object to be imaged, and the flip angle is set such that prespecified target contrast for the two tissue types is obtained at the set repetition time.

13 Claims, 4 Drawing Sheets

(51) Int. Cl.
  *A61B 5/00*   (2006.01)
  *A61B 5/113*  (2006.01)
  *A61B 5/024*  (2006.01)
  *A61B 5/055*  (2006.01)
  *A61B 5/318*  (2021.01)

(52) U.S. Cl.
  CPC ..... *G01R 33/4828* (2013.01); *G01R 33/5617* (2013.01); *G01R 33/56509* (2013.01)

(56) References Cited

U.S. PATENT DOCUMENTS

| | | | |
|---|---|---|---|
| 5,781,010 A * | 7/1998 | Kawasaki | G01R 33/5673 324/306 |
| 2005/0119554 A1 | 6/2005 | Jenniskens et al. | |
| 2008/0262339 A1* | 10/2008 | Garwood | A61B 5/055 600/413 |
| 2019/0310339 A1 | 10/2019 | Fautz et al. | |

OTHER PUBLICATIONS

Elster, Allen D.:, "Cardiac gating parameters", in: Questions Answers in MRI/ Elster LLC, https://web.archive.org/web/20171217154822/ https://mriquestions.com/gatingparameters.html (2017).

Mugler III, John P.:, "Optimized three-dimensional fast-spin-echo MRI", Journal of Magnetic Resonance Imaging, vol. 39, No. 4, pp. 745-767 (2014).

European Search Report for German Application No. 2018P02210 dated Jun. 18, 2020.

\* cited by examiner

METHOD AND APPARATUS FOR TRIGGERING MAGNETIC RESONANCE RECORDINGS WITH OBJECT MOVEMENTS

BACKGROUND OF THE INVENTION

Field of the Invention

The present invention concerns a method for obtaining magnetic resonance (MR) raw data for an MR image of the type wherein spin-echo-based imaging includes applying a static magnetic field in the positive z-direction, as a result of which magnetization of nuclei in the positive z-direction is obtained in an object to be imaged, applying (90°) excitation pulse, as a result of which the magnetization is tilted by a predetermined angle, applying a refocusing pulse, and applying an RF pulse at the point in time of an echo caused by the pulses as a result of which the magnetization is deflected in the negative z-direction by a flip angle. The present invention also concerns an MR apparatus.

Description of the Prior Art

Magnetic resonance imaging (MRI) is a known imaging modality in medical engineering. An examination object, for example a patient, is exposed to a substantially static magnetic field, on which is impressed or superimposed a similarly substantially static, i.e. temporally constant, gradient, i.e. a spatially linearly increasing gradient field. Then, radio-frequency (RF) pulses, i.e. an alternating magnetic field, are radiated with which nuclear spins are excited resonantly in the examination object. The RF pulses are generated by an RF amplifier and a coil supplied or driven thereby, such as a so-called body coil. The parts of the examination object in which excitation of the nuclear spins occurs is dependent on the local strength of the effective, static magnetic field and the frequency of the RF pulses. Appropriate variation can therefore achieve targeted selective excitation of a slice of the examination object. Thus, a number of RF pulses are radiated in succession, i.e. in a sequence or measuring sequence, and the recording of respective response or relaxation signals (MR signals, raw data) enables a three-dimensional recording of the examination object to be obtained.

The static magnetic field causes alignment of the dipole moments of the examination object in the field direction (z-direction). This results in externally measurable magnetization in the direction of the external static field (longitudinal magnetization). An alternating magnetic field with a suitable frequency, strength and duration (in the present case, also called excitation pulse or 90° excitation pulse), can tip the magnetization out of the longitudinal direction (z-direction) such that it precesses in the x-y plane and the longitudinal magnetization initially has the value 0. After the (90°) excitation pulse, the longitudinal magnetization is restored—this is called spin-lattice relaxation. The time constant for this spin-lattice relaxation is designated T1.

The spin-echo technique is based on a sequence of a (90°) excitation pulse and a refocusing pulse. In order to prevent the influence of interfering magnetic fields on the precessing spins (which leads to reduced synchronization between the gyroscopic motions of the individual spins and thus accelerates lateral relaxation), the refocusing pulse is radiated in the middle of the time interval between the (90°) excitation pulse and the data readout (half echo time). This pulse causes synchronization of the gyroscopic motions resulting in maximum signal amplification (echo) at the point in time of the data readout (echo time TE).

The turbo-spin-echo (TSE) technique is a development of the spin-echo technique. Whereas during the spin-echo sequence, an echo is read out on each excitation (90° pulse), with the TSE technique, a number of echoes are generated and received (echo train or pulse train) on each excitation by additional refocusing pulses. These multiple echoes can greatly reduce the measuring time or achieve higher resolution than is the case with the SE technique.

Spin-echo-based, T1-weighted imaging is a widely used standard for neuroimaging, spinal imaging and musculoskeletal (MSK) imaging. Such recordings are particularly subject to interference from artifacts caused by pulsatile blood flow. The bright signal from pulsating blood results in flow artifacts along the phase encoding direction that are superimposed on other tissues or lesions. Other artifacts can be caused by other movements of the object or patient. For example, in addition to blood or cerebrospinal fluid flow, other direct causes of physiological artifacts are heartbeat, respiration, eye movement, autonomous movements, such as peristalsis and swallowing, and other movements.

A fundamental possibility for reducing flow artifacts is to trigger recording with the heart rate or the ECG signal. Typical trigger times with a normal heart rate are 700 ms to 1000 ms (corresponding to 85 to 60 heartbeats/minute). At 600 ms to 900 ms (at three tesla), the repetition times TR desired for the T1 contrast in T1-weighted SE or TSE imaging are only slightly shortly than typical trigger times. However, when T1-weighted recording is triggered, the TR, and hence the T1 contrast, is determined by the patient's heart rate and is no longer freely selectable.

The conventional solution has been, for example, to dispense with triggers in normal T1-weighted anatomical imaging (i.e. for the depiction of soft tissue, not for the depiction of vessels). Attempts are made to reduce flow artifacts by flow compensation or by the use of weak diffusion gradients that suppress the signal from flowing blood. However, each of these methods has weak points, such as general sensitivity to motion or incomplete reduction of flow artifacts.

SUMMARY OF THE INVENTION

An object of the present invention is to reduce the influence of artifacts caused by movements of the object to be examined during MR imaging.

According to the invention, this object is achieved by a method for obtaining a measuring signal for an MR image for spin-echo-based imaging by applying a static magnetic field in the positive z-direction as a result of which magnetization in the positive z-direction is obtained in an object to be imaged, applying a (90°) excitation pulse as a result of which the magnetization is tilted by a predetermined angle, applying a refocusing pulse and applying an RF pulse at the point in time of an echo caused by the excitation and refocusing pulses, as a result of which the magnetization is deflected in the negative z-direction by a flip angle, detecting a movement of the object to be imaged, prespecifying a target contrast for two tissue types of the object, setting a repetition time (TR) of the (90°) excitation pulse in dependence on the movement of the object to be imaged, and setting the flip angle such that the prespecified target contrast for the two tissue types is obtained at the set repetition time.

Consequently, according to the present invention, MR signals (raw data) are obtained for reconstructing an MR image in that, first, different magnetic fields are applied to the examination object (object for short). The measuring signal is in particular obtained from the spin-echo technique. Then, an MR image or an MR recording is generated from the measuring signal or a plurality of measuring signals. As stated, a static magnetic field $\vec{B}_0$ is applied in the positive z-direction. As a result, magnetization in the positive z-direction is established in the object.

Furthermore, for example, a (90°) excitation pulse is applied in the MRI scanner. This tilts (flips) the magnetization, which thus far was aligned in the positive z-direction, by 90° or another angle so that a magnetization component forms in the x-y plane. From this position, the magnetization vectors diverge in the x-y plane around the z-axis. Now, typically, a refocusing pulse or a gradient field for refocusing or rephasing is applied for half the echo time. After refocusing, the previously divergent magnetization vectors reconverge so that, after the same time interval as that between the (90°) excitation pulse and the refocusing pulse has elapsed, the magnetization vectors are back in phase (rephasing). At this point in time, they produce a clear maximum of the induced signal, namely the spin echo.

A further RF pulse is also applied at the point in time of the echo induced by the pulses. Thus, the magnetization vectors are now in phase and are swiveled by an angle to be determined (flip angle) in the negative z-direction. The flip angle is, for example, selected such that a specific contrast results at a prespecified repetition time (TR) of the (90°) excitation pulse for two predetermined tissue types of the object to be examined. This means that a specific contrast is established in that the flip angle is changed appropriately without changing the repetition time. Thus, in addition to the setting option by means of repetition time, there is another degree of freedom available for setting the contrast.

Preferably, the movement of the object to be imaged is measured simultaneously with the application of the magnetic fields. This movement is, for example, the heartbeat, pulsatile blood, respiration or the like. This means, therefore, that generally, it is not the entire object that moves, but only a part thereof. For example, the movement is a rhythmic or periodic movement.

A target contrast is prespecified for the object's two tissue types. For example, a predetermined contrast between the respective recording regions is desired as a target contrast for the gray and white brain tissue. In the simplest case, the prespecification consists in the use of a specific contrast as given.

To trigger the MR recording, the repetition time TR of the (90°) excitation pulse or the entire pulse train is set in dependence on the movement of the object to be imaged. This means that the repetition frequency of the (90°) excitation pulse corresponds, for example, to the motion frequency of the object to be imaged. However, the repetition time of the (90°) excitation pulse can also be an integer multiple or a predetermined fraction of a cycle time of the movement of the object to be imaged. In any case, the repetition time of the (90°) excitation pulse is triggered by the movement of the object to be imaged.

Finally, the flip angle is set such that the prespecified target contrast for the two tissue types is obtained at the set repetition time. This means that the flip angle is set in dependence on the movement of the object. For example, the flip angle is dependent on the patient's heart rate. If the repetition time triggered by the movement of the object at a specific target contrast is to be used, it is accordingly necessary to set the flip angle in a suitable manner. Therefore, with a fixed contrast, the flip angle is changed with the movement of the object. As a result, in particular the T1 contrast is no longer prespecified in a fixed manner by the heart rate of the patient but is freely selectable within certain limits.

In a preferred embodiment, the prespecification of the target contrast takes place by a contrast being calculated using the specific T1 and T2 values for the two tissue types as the target contrast for a prespecified model repetition time. Although it is possible to prespecify a special target contrast value for fixed tissue pairs, such as gray and white brain tissue, for other user-selected tissue pairs, it is possible to calculate a target contrast value of this kind using the specific T1 and T2 values. This provides a high degree of flexibility.

In a particular embodiment of the method, the movement of the object is based on respiration. If, for example, images are to be recorded of a part of a patient, in particular the ribcage region, it can be advantageous to match the repetition time to the respiration. Therefore, the repetition time can be triggered with a signal representing the respiration. It is not mandatory for the repetition time to correspond to the respiratory period. Instead, it is also possible for a multiple of the repetition time to be assigned to a respiratory period. The individual recordings should then be assigned to the respective segment of a period. Under some circumstances, it is also possible to use only a part of the respiratory period for the recordings, for example the first half or the first quarter of a respiratory period.

In a preferred embodiment, the movement of the object is based on a heartbeat. Since usually the heart rate is in the range of the repetition frequency of the SE or TSE pulse trains, it is particularly advantageous for these pulse trains to be triggered with the heart rate or the heartbeat.

A preferred time range for the repetition times TR in T1-weighted SE or TSE imaging with a magnetic flux density of three tesla is between 600 and 900 ms. Typical heartbeat periods also lie within this time range. Therefore, it is advantageous to trigger the repetition time TR directly with the heartbeat.

The heartbeat can be measured, for example, by ECG or pulse measurement. A trigger signal for SE or TSE pulse trains can be obtained from these signals. For example, the corresponding pulse train can be started each time a heartbeat takes place or starts.

According to a further embodiment, the repetition time corresponds to a mean time between two consecutive heartbeats in a number of heartbeat intervals. This means that a plurality of heartbeat intervals or heartbeat periods are averaged and the SE or TSE pulse train is only triggered with the corresponding average time or that the repetition time of the pulse train is set with this averaged time. By means of this averaging, it is possible to ensure that the repetition time does not change excessively and that in particular short changes to the heart intervals do not directly affect the repetition time.

In a further embodiment, the two prespecified tissue types of the object are white and gray brain tissue and, accordingly, the contrast is a gray-white contrast. This means that the flip angle is used to enable a specific contrast to be set with brain recordings. In particular, the gray-white contrast can be maximized with brain recordings. Obviously, the same also applies for other tissue types. For example, it is possible to maximize the contrast between cartilage tissue and muscle tissue or bone tissue and cartilage tissue.

In another preferred embodiment, the flip angle is dynamically adapted to the movement of the object to be imaged. This means that the flip angle of the movement of the object to be imaged is tracked. Therefore, the movement of the object to be reproduced is recorded continuously and, for example, a corresponding motion signal is used to update the flip angle continuously. In this way, it is possible to adapt the flip angle to a changed heart rate. If, for example, during an examination, a patient's pulse rate rises and the repetition time is synchronized with the pulse rate (i.e. the repetition time falls), it is also necessary to reduce the flip angle so that, for example, the gray-white contrast for brain tissue can be kept at a maximum. Thus dynamic adaptation enables the contrast to be kept at a maximum in each instantaneous situation. However, the flip angle can optionally be changed in dependence on the instantaneous repetition time such that the contrast, for example the gray-white contrast, is kept constant.

Furthermore, after the (90°) excitation pulse, the refocusing pulse can be preceded by at least one further refocusing pulse. This means that a sequence of one excitation pulse and a plurality of refocusing pulses is applied thus resulting in a pulse train. As a result, it is possible to implement the turbo-spin-echo technique, wherein a plurality of echoes is obtained in such a sequence.

The predetermined angle by which the magnetization is tilted by the excitation pulse can be within a range of 90°+/−45°. However, in principle, this amount can be less than 45°.

Furthermore, the magnetization can in each case be tilted by 180° or less with the refocusing pulse or the at least one further refocusing pulse ($\alpha 2, \ldots, \alpha n$). In particular for reasons of energy efficiency, angles of, for example, 120° or 150° are also suitable.

According to the invention, the above-described object is also achieved by an MR apparatus for obtaining a measuring signal for an MR image for spin-echo-based imaging, which has an MR data acquisition scanner that includes a first magnetization arrangement that applies a static magnetic field in the positive z-direction in the scanner, as a result of which magnetization in the positive z-direction is obtained in an object to be imaged, and a second magnetization arrangement that applies a (90°) excitation pulse, as a result of which the magnetization is tilted by a predetermined angle in the object, and that also applies a refocusing pulse and an RF pulse at the time of an echo caused by the excitation and refocusing pulses, as a result of which the magnetization is deflected in the negative z-direction by a flip angle. The MR apparatus also includes a movement detector that detects a movement of the object to be imaged. The second magnetization arrangement sets a repetition time (TR) of the (90°) excitation pulse in dependence on the movement of the object to be imaged, and the second magnetization arrangement sets the flip angle such that a predetermined target contrast for two tissue types is obtained at the set repetition time.

Therefore, the magnetization arrangements of the MR scanner are used to apply the magnetic fields or magnetic field pulses and in particular an SE or TSE pulse sequence. A motion detectors is used to measure the movement of the object to be imaged. If the movement is, for example, the heartbeat, the motion detector can be implemented as an ECG device or pulsimeter. However, the motion detector can also be any other type of sensor able to detect movements of the object or patient. The second magnetization arrangement then interacts with the motion detector by setting the repetition time in dependence on the movement of the object and also adjusts the flip angle again in dependence on the repetition time.

The above advantages and possible variations described in connection with the method according to the invention also apply analogously to the MR apparatus according to the invention.

DESCRIPTION OF THE PREFERRED EMBODIMENTS

By way of example, brain tissue is to be examined in an MR system. However, it is also possible to examine other tissue types. Spin-echo-based, T1-weighted imaging is selected, for example. The following examples relate to turbo-spin-echo techniques, but they can also be implemented analogously with simple spin-echo techniques.

Figure 1:
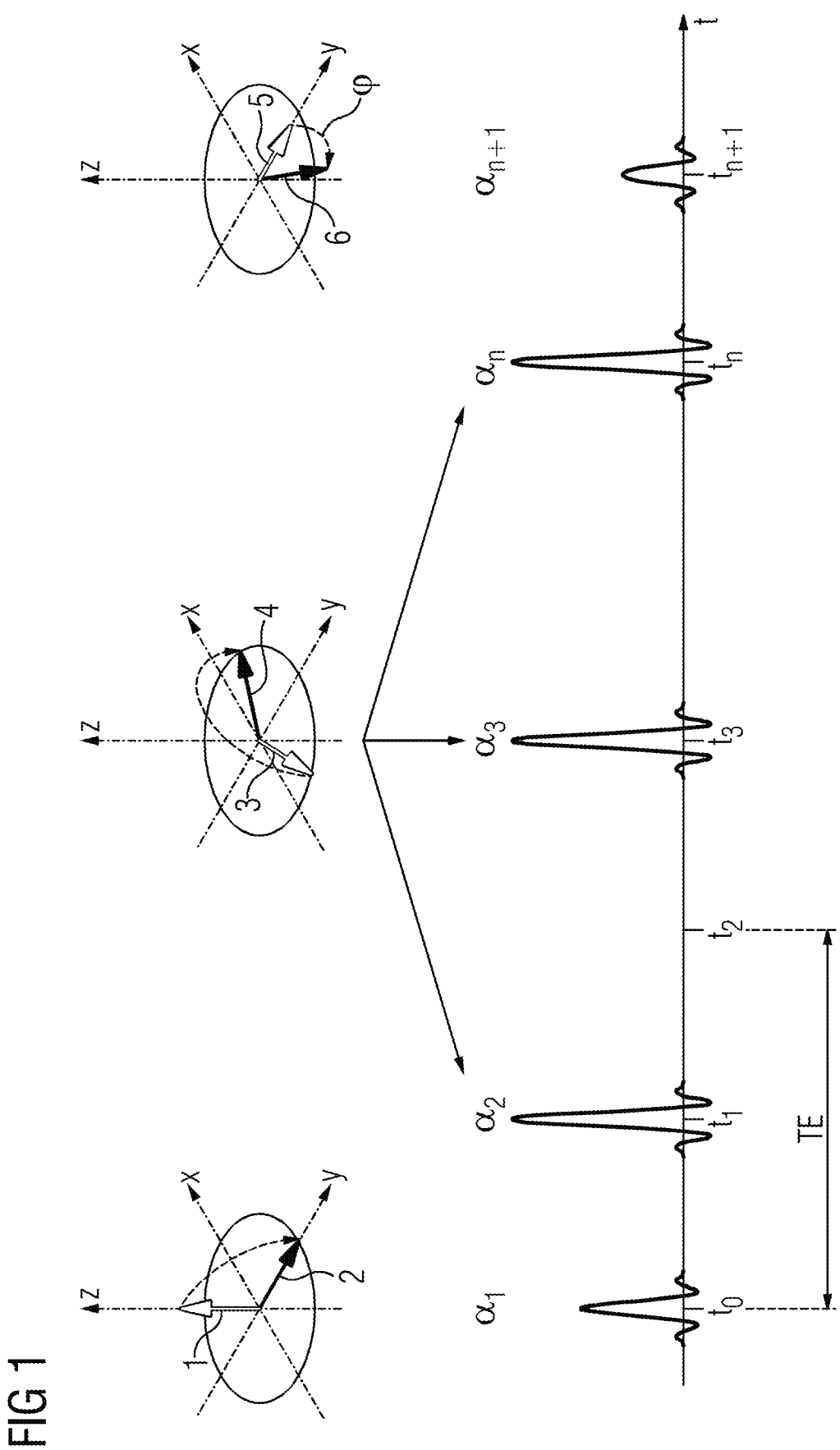
FIG. 1 shows a pulse sequence according to the present invention with a settable flip angle.

According to FIG. 1, a spin ensemble of an atom nucleus, and hence the magnetization 1 of an affected object, is first aligned in the z-direction. To this end, a static magnetic field is applied to the object in the z-direction (longitudinal direction). At a point in time t0, a (90°) excitation pulse $\alpha 1$ is applied to the object. As a result, the magnetization is tilted by a predetermined (settable) angle, which can be 90°, or also more or less than this. Hence, at least one component of the corresponding magnetization vector is in the x-y plane. This results in magnetization 2 tilted by 90°. This tilted magnetization 2 is now perpendicular to the direction of the static magnetic field. The individual magnetization vectors of the tilted magnetization 2 now diverge clockwise and counterclockwise about the z-axis. Herein, the individual magnetization vectors have different speeds. The magnetization vectors are dephased.

In order to now achieve rephasing or refocusing, one or more refocusing pulses $\alpha 2, \alpha 3, \ldots, \alpha n$ are applied. The effect of such refocusing is depicted in FIG. 1 for the refocusing pulse $\alpha 3$ specifically for an individual magnetization vector 3. Here, this is tilted by 180° for example about the y-axis, as a result of which the magnetization vector 4 tilted by 180° is obtained in the x-y plane. The tilting can also take place with a different angle, but then a corresponding component is also obtained in the x-y plane. This tilted or refocused component then returns to the starting position, here the y-axis corresponding to the tilted magnetization 2 after the (90°) excitation pulse. All other spins in the x-y plane are also tilted by 180° or the corresponding angle and also return at their speed to the starting position. Hence, the refocusing pulse causes synchronization of the individual magnetization vectors since at a point in time t2 these meet again in said starting position and herein generate the so-called spin echo. Therefore, the point in time t2 corresponds to the echo time. The echo time TE represents a time interval between the time t0 of the (90°) excitation pulse $\alpha 1$ and the echo time t2. The point in time t1 of the refocusing pulse α2 lies exactly between the two point in times t0 and t2, since, after the refocusing, the magnetization vectors again require exactly the same time for rephasing as for dephasing.

In the present example, the further refocusing pulses α3 and αn occur at the point in times t3 and tn. The number of refocusing pulses can be selected as required. However, it must be at least one.

The last echo of the TSE echo train occurs with a time interval of TE/2 after the time tn, i.e. at the point in time tn+1. Now, according to the invention, at exactly this point in time, an RF pulse αn+1 is applied which deflects the remaining transverse magnetization 5, which has decreased slightly compared to the tilted magnetization 2 due to losses, toward the negative z-axis as a result of which flipped magnetization 6 is obtained. The flip angle φ between the remaining transverse magnetization 5 and the flipped magnetization 6 can be set by the RF pulse αn+1, which can also be referred to as the "after-train pulse"

Therefore, the "after-train pulse" can achieve contrast modification. This is in particular particularly useful if the repetition time is based on movements of the object or patient. Without the "after-train pulse", the contrast of the MR images (for example gray-white contrast between gray and white brain tissue) would substantially only change due to the movement or repetition time. With the "after-train pulse", the contrast can also be changed by the flip angle φ.

Figure 2:
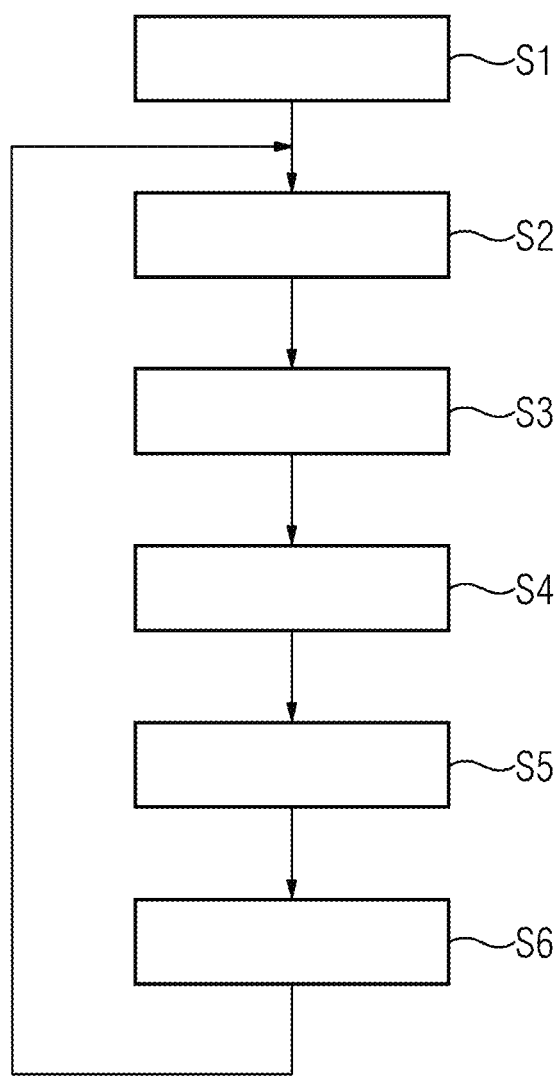
FIG. 2 is a flowchart of the method according to the invention.

FIG. 2 shows a corresponding method sequence in which the repetition time is triggered by a movement of the object and a specific target contrast is to be achieved. In a first method step S1, a static magnetic field is applied to the object in the positive z-direction so that magnetization in the positive z-direction occurs in the object to be imaged. In addition, to obtain a measuring signal for an MR image for spin-echo-based imaging, a pulse train is applied according to step S2. Herein, first, a (90°) excitation pulse is applied as a result of which the magnetization of the nuclei in the object is tilted by a predetermined angle, for example 90 degrees. After a predetermined time, a refocusing pulse is applied. At the same time after the refocusing pulse, an RF pulse is applied at the point in time of an echo caused by the pulses, as a result of which the magnetization is deflected in the negative z-direction by a predetermined flip angle.

Simultaneously with or in close temporal relation to the application of the pulse train in step S2, there is a detection of a movement of the object to be imaged in step S3. Although, in FIG. 2, the step S3 is shown as after step S2, this step can also take place before step S2 or simultaneously with step S2. In this step S3, for example the movement of the object or a part of the object due to the heartbeat, respiration, eye movement etc. is identified by suitable sensors.

In a further step S4, a target contrast for two tissue types of the object is prespecified. Although in the example in FIG. 2, this step S4 takes place after step S3, it can also take place at the beginning of the method or before or after the above steps S1 to S3 or simultaneously therewith. On the prespecification of the target contrast, a corresponding value can, for example, be read from a table and used for the method. Alternatively, however, the target contrast can be prespecified by calculating it in advance for a specific tissue pair in a specific way.

In a subsequent step S5, a repetition time TR of the (90°) excitation pulse is set in dependence on the movement of the object to be imaged. Therefore, the repetition time is, for example, triggered with the movement of the object to be imaged or with synchronized therewith.

In a subsequent step S6, the flip angle is set such that the prespecified target contrast from step S4 is obtained for the two tissue types at the set repetition time. The setting of the flip angle can be performed once or tracked dynamically. If, for example, the repetition time changes constantly, for example with changes to the patient's pulse rate, the flip angle can be correspondingly tracked dynamically so that the contrast can be retained. Finally, the set flip angle is used again to apply the pulse train including the "after-train pulse" in step S2.

Figure 3:
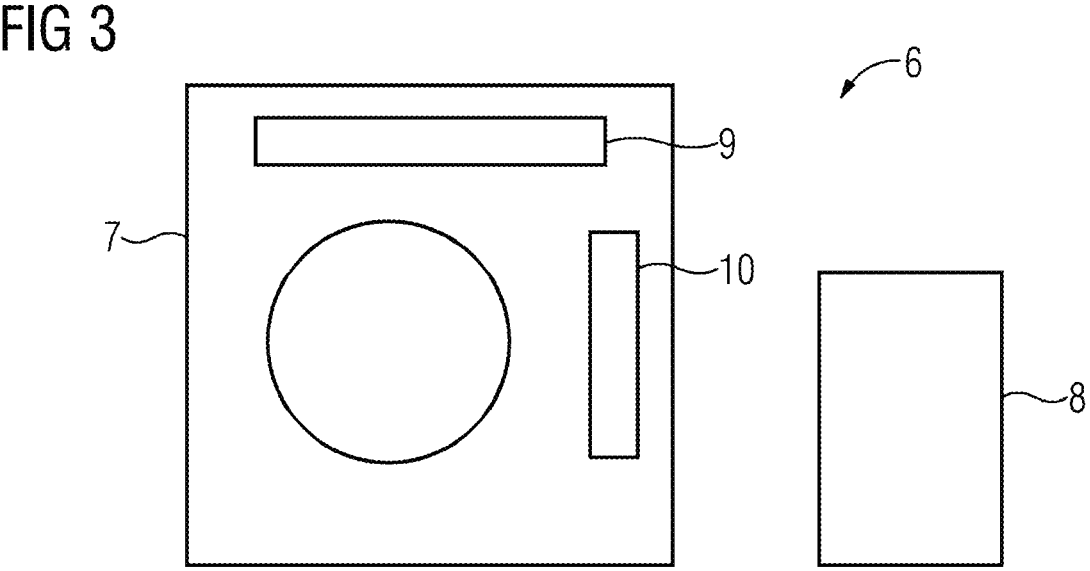
FIG. 3 is a block diagram of an MR apparatus according to the invention.
Figure 4:
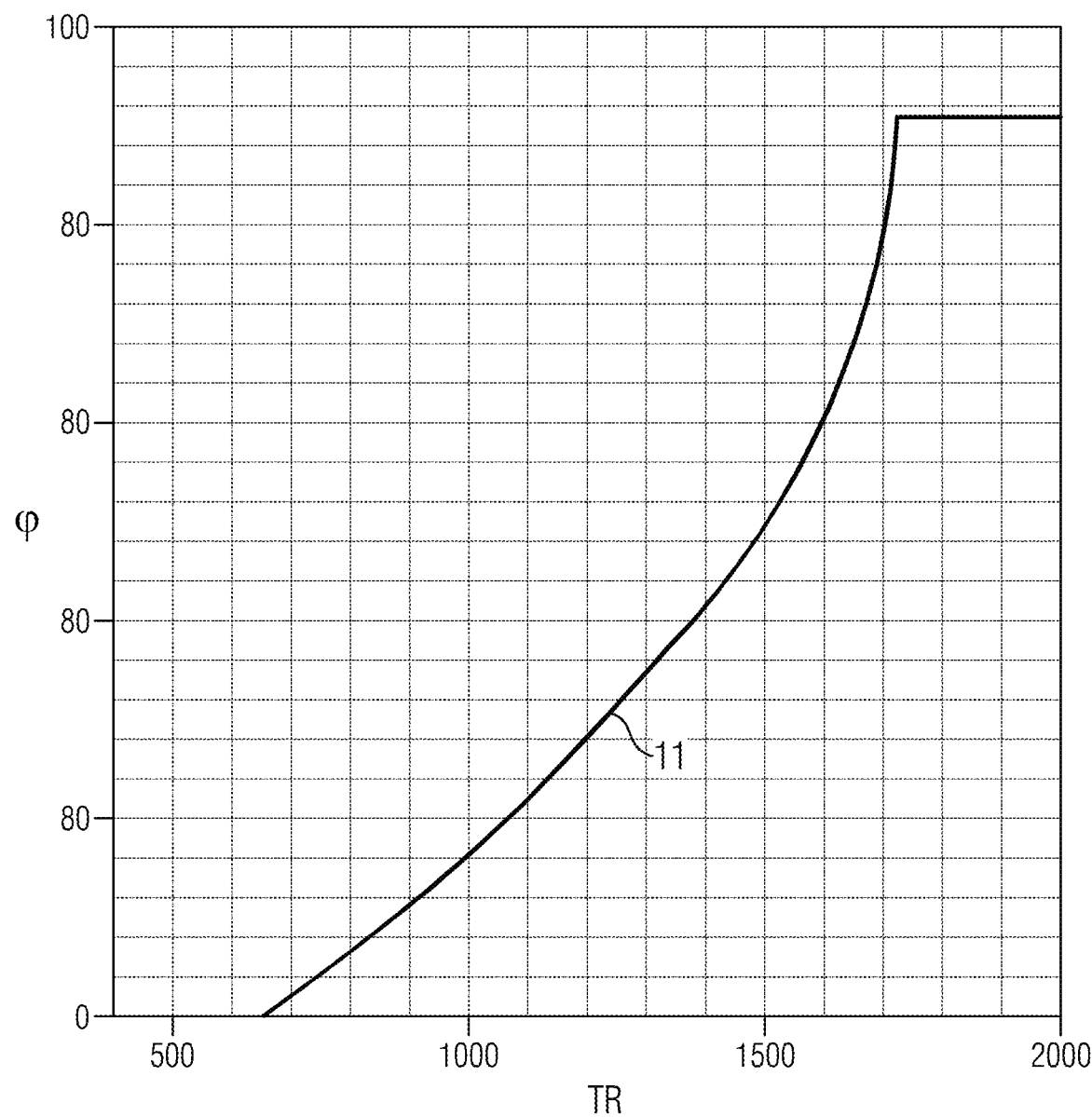
FIG. 4 is a diagram of the flip angle versus the repetition time TR for maximum gray-white contrast.

FIG. 3 is a block diagram of an MR apparatus 6. The MR apparatus 6 has an MR data acquisition scanner 7 and a motion detector 8. Optionally, the scanner 7 and the motion detector 8 can be integrated in a common housing. The scanner 7 performs the actual MR examination. It has a first magnetization arrangement 9 and a second magnetization arrangement 10. The first magnetization arrangement 9 applies the static magnetic field and the second magnetization arrangement 10 applies the pulse train.

The motion detector 8 is, for example, an ECG device or a pulsimeter. However, the motion detector 8 can also be any other types of sensor for detecting a movement of an object or partial object, such as respiration, eye movement, etc. A signal from the motion detector 8 is provided to the second magnetization arrangement 10 in order to trigger the pulse train or set the repetition time. In dependence on this, the second magnetization arrangement 10 optionally automatically sets the flip angle for a predetermined contrast of a tissue pair.

The optimum flip angle φ for each TR that results in maximum contrast is shown in FIG. 3 by the curve 11. It rises steadily after about 650 ms from the flip angle equal to 0° and, after about 1700 ms, reaches the flip angle 90°, which is optimum here. While, therefore, the gray-white contrast for increasing TR greater than 1100 ms conventionally decreases (see FIG. 5, curve 12), with an increasing "after-train" flip angle φ, the gray-white contrast can be further increased.

For example, to calculate the optimum "after-train" flip angle, it is for example possible to calculate the signals for the TSE sequence of the tissue of interest or the tissue pair of interest by means of known algorithms, for example for all integer flip angles from 0 to 90°. Such an algorithm can be a so-called "phase-graph" algorithm or another algorithm for solving the Bloch equation. The signal amplitudes for the different tissues can be used to calculate the contrast and identify the flip angle φ resulting in the maximum contrast.

In many cases, it is not important always to achieve the maximum contrast. Rather, it may also be desirable to keep a contrast constant when the repetition time TR changes. For example, the repetition time may be extended to reduce the stress on the patient or reduce energy consumption, while at the same time the contrast is to be retained. In such a case, the above-described calculation of the optimum "after-train" flip angle can be used to determine the flip angle for a specific TR that generates a contrast that is as similar as possible to the contrast that is generated at another TR (and possibly another flip angle or flip angle 0).

Figure 5:
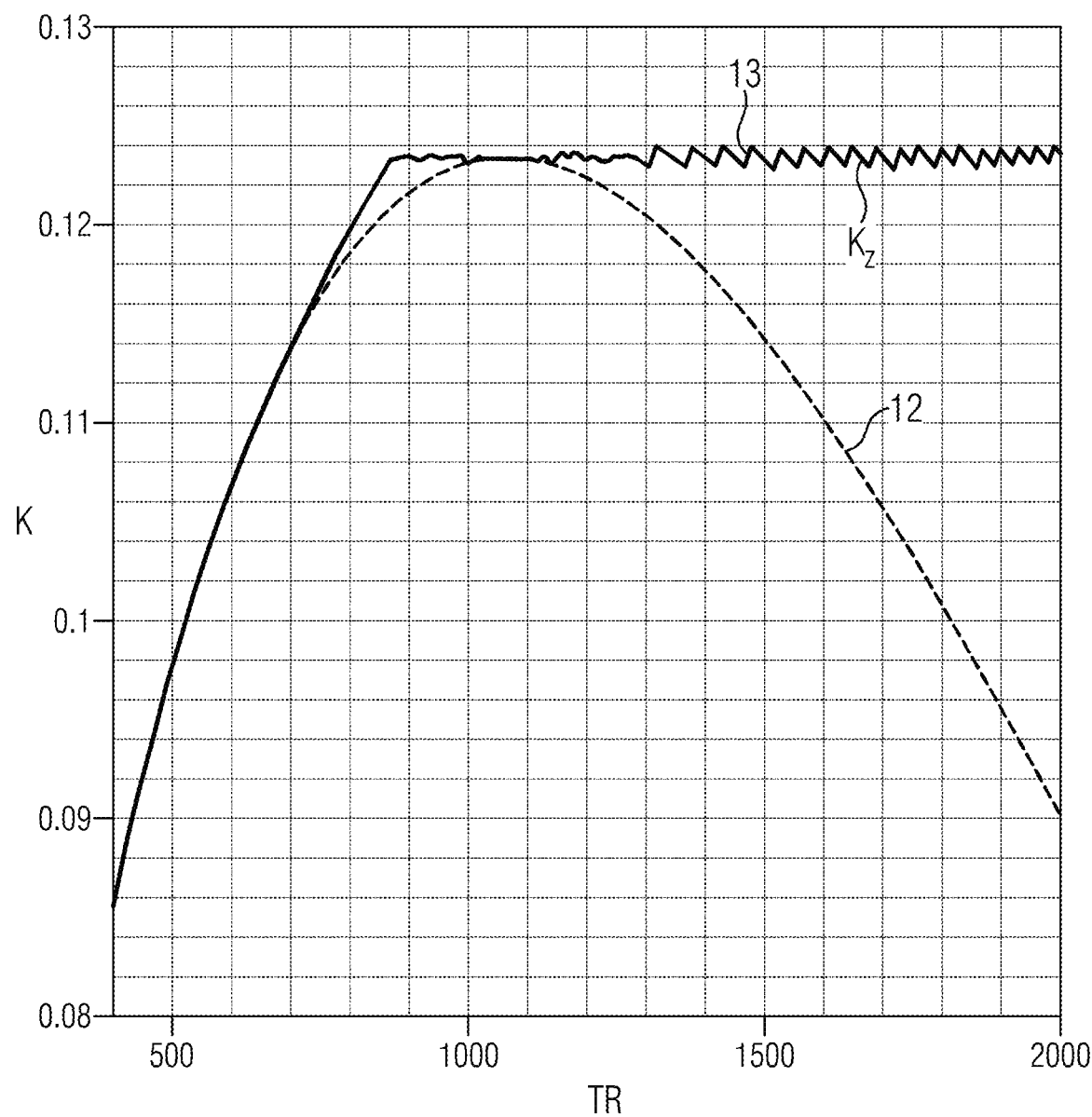
FIG. 5 is a diagram of the gray-white contrast versus the repetition time TR, wherein the flip angle is changed such that the contrast remains constant.

To this end, FIG. 5 shows the gray-white contrast, which represents a measuring signal to be obtained, over the repetition time TR of about 500 to 2000 ms. For purposes of comparison, a curve 12 for a conventional TSE sequence without an "after-train pulse" is depicted. Over the repetition time, as described above, the contrast K, first increases and then falls off again. The curve 13 shows the gray-white contrast for a TSE-sequence with an "after-train pulse", wherein the contrast with different flip angles φ can be kept substantially constant over specific range of TR (here about 900 to 2000 ms). Therefore, the flip angle φ will always be selected in dependence on the TR such that a target contrast Kz is achieved.

The prespecification of the contrast can thus be in order to keep the contrast constant at a specific value, for example target contrast Kz, independently of the heartbeat. In this case, the flip angle is then adapted to the repetition time TR synchronized with the heartbeat such that, for example, the gray-white contrast remains constant. According to the invention, therefore, the contrast modification can be used by means of the flip angle, for example, to enable ECG-triggered recordings without thereby the T1-contrast being (exclusively) defined by the time between two heartbeats. A concrete method sequence can be summarized once again as follows:

1. A prespecified TR is used to calculate the contrast between two tissue types (for example gray and white brain tissue) for the corresponding frequency, for example on the basis of the tissue-specific T1 and T2 values. This defines the target contrast.

2. An ECG or pulse measurement is used to determine the mean duration between two heartbeats. This duration defines the TR* actually implemented in a triggered recording.

3. The flip angle of the "after-train pulse" is determined such that, at the mean interval between two heartbeats TR*, the contrast between the two predetermined tissue types corresponds to that achieved at the set TR without an additional "after-train pulse".

4. A feedback loop can be used to adapt the flip angle gradually if the TR* changes over the duration of the measurement. Herein, excessively large jumps in the flip angle should be avoided in order not to disturb the T1 steady state. Tracked or rolled averaging over a plurality of heartbeat intervals is recommended.

Advantageously, therefore, the invention, enables T1-weighted TSE recordings to be obtained, wherein the T1 contrast (between two predefined tissue types) is prespecified independently of the patient's heartbeat by a selectable target TR.

Hence, according to the invention, it is possible to provide an MR device with a first magnetization arrangement used to apply the static magnetic field and a second magnetization arrangement embodied to apply the SE or TSE sequence including the "after-train pulse" with the specific flip angle triggered with the measuring arrangement. This specific flip angle is set in accordance with the above specifications.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for obtaining raw data for reconstructing a magnetic resonance (MR) image, comprising:
   operating an MR data acquisition scanner to apply a static magnetic field in a positive z-direction in the scanner, which produces magnetization in the positive z-direction in an object situated in the scanner;
   operating said MR data acquisition scanner so as to execute a spin-echo-based MR data acquisition sequence including applying an excitation pulse that tilts said magnetization by a predetermined angle;
   in said spin-echo-based sequence, applying a refocusing pulse;
   operating said MR data acquisition scanner to additionally apply an RF pulse at a time of an echo caused by said excitation and refocusing pulses, which deflects said magnetization in a negative z-direction by a flip angle;
   detecting a movement of said object using a motion detector;
   providing a computer with a predetermined target contrast for two tissue types in said object;
   in said computer, setting a repetition time of said excitation pulse in said spin-echo-based sequence based on the detected movement of the object; and
   in said computer, setting the flip angle in said spin-echo-based sequence so that said predetermined target contrast for said two tissue types is obtained at the repetition time that has been set, wherein the flip angle is dynamically adapted based on the detected movement of the object.

2. A method as claimed in claim 1 comprising calculating a contrast for a predetermined model repetition time, using specific T1 and T2 values respectively for said two tissue types, the calculated contrast being provided as the predetermined target contrast.

3. A method as claimed in claim 1 wherein the detected movement of the object is a respiration-produced movement of the object.

4. A method as claimed in claim 1 wherein the detected movement of the object is a heartbeat-produced movement of the object.

5. A method as claimed in claim 4 wherein the heartbeat-produced movement is a heartbeat obtained by an electrocardiogram (ECG), or by detecting a pulse of said object.

6. A method as claimed in claim 4 wherein the repetition time is determined based on a mean time between two consecutive heartbeats, in a plurality of heartbeat intervals.

7. A method as claimed in claim 1 comprising specifying, as said two tissue types of the object, white brain tissue and gray brain tissue, and wherein said contrast is a gray-white contrast.

8. A method as claimed in claim 1 comprising, after said excitation pulse, preceding said refocusing pulse with at least one further refocusing pulse.

9. A method as claimed in claim 1 comprising setting said predetermined angle by which said magnetization is tilted by said excitation pulse to be within a range of 45° to 135°.

10. A method as claimed in claim 1 comprising tilting said magnetization by 180° or less with said refocusing pulse.

11. A method as claimed in claim 1 comprising, after said excitation pulse, preceding said refocusing pulse with at least one further refocusing pulse, and tilting said magnetization by 180° or less with said refocusing pulse or said at least one further refocusing pulse.

12. A method as claimed in claim 1 wherein the repetition time of said excitation pulse in said spin-echo-based sequence is set based on a cycle time of the detected movement of the object.

13. A magnetic resonance (MR) apparatus comprising:
   an MR data acquisition scanner;
   a computer configured to operate said MR data acquisition scanner:
      so as to apply a static magnetic field in a positive z-direction in the scanner, which produces magnetization in the positive z-direction in an object situated in the scanner;
      so as to execute a spin-echo-based MR data acquisition sequence including applying an excitation pulse that tilts said magnetization by a predetermined angle;

in said spin-echo-based sequence so as to apply a refocusing pulse; and so as to additionally apply an RF pulse at a time of an echo caused by said excitation and refocusing pulses, which deflects said magnetization in a negative z-direction by a flip angle; and a motion detector configured to detect a movement of said object and provide a signal to said computer that represents the detected movement, wherein:

the computer is provided with a predetermined target contrast for two tissue types in said object; and the computer is further configured to:

set a repetition time of said excitation pulse in said spin-echo-based sequence dependent on the detected movement of the object; and set the flip angle in said spin-echo-based sequence so that said predetermined target contrast for said two tissue types is obtained at the repetition time that has been set, wherein the flip angle is dynamically adapted based on the detected movement of the object.

* * * * *